US009080999B2

(12) United States Patent
Osipchuk et al.

(10) Patent No.: US 9,080,999 B2
(45) Date of Patent: Jul. 14, 2015

(54) VOLTAGE OFFSET CORRECTION IN HIGH-THROUGHPUT ELECTROPHYSIOLOGICAL MEASUREMENT SYSTEM

(75) Inventors: Yuri V. Osipchuk, Foster City, CA (US); Philip Churchward, Victoria (AU); Keith Thomas, Aurora, CO (US)

(73) Assignee: Molecular Devices, LLC, Sunnyvale, CA (US)

( * ) Notice: Subject to any disclaimer, the term of this patent is extended or adjusted under 35 U.S.C. 154(b) by 695 days.

(21) Appl. No.: 13/453,645

(22) Filed: Apr. 23, 2012

(65) Prior Publication Data
US 2013/0060478 A1 Mar. 7, 2013

Related U.S. Application Data (60) Provisional application No. 61/530,732, filed on Sep. 2, 2011.

(51) Int. Cl.
*G01N 27/327* (2006.01)
*G01N 33/487* (2006.01)
(52) U.S. Cl.
CPC .................. *G01N 33/48728* (2013.01)
(58) Field of Classification Search
CPC ................................. G01N 33/48728
See application file for complete search history.

(56) References Cited

U.S. PATENT DOCUMENTS 7,270,730 B2 9/2007 Schroeder et al.
2011/0251102 A1 10/2011 Osipchuk et al.

OTHER PUBLICATIONS

User's Guide for Works® Quattro published by Molecular Devices Corporation, Part # 0112-0125 Rev. A, 2005, 142 pages long.*
Discussion of IonWorks Voltage Offsets, Automated E-Phys User Meeting Biophysics 2009, James Costantin, 18 pages long.*
Reichenbächer and J. W. Einax, Challenges in Analytical Quality Assurance, Springer-Verlag Heidelberg 2011, Chapter 2, pp. 7-35.*

* cited by examiner

Primary Examiner — Alex Noguerola
(74) Attorney, Agent, or Firm — Bella Fishman (57) ABSTRACT

A computer-implemented method for controlling command voltages applied to electrodes during an electrophysiology measurement procedure using a high-throughput measurement system is provided. An initial command voltage is applied to the electrodes to obtain baseline currents respectively associated with the electrodes. A common offset voltage is determined based on the baseline currents, and an adjusted command voltage is determined based on the initial command voltage and the common offset voltage. The adjusted command voltage is applied to at least one of the electrodes to obtain an adjusted current measured by the electrode. A local offset voltage for the electrode is determined based on the adjusted current measured by the electrode. A subsequent command voltage applied to the electrode incorporates the common offset voltage and the local offset voltage.

15 Claims, 6 Drawing Sheets

VOLTAGE OFFSET CORRECTION IN HIGH-THROUGHPUT ELECTROPHYSIOLOGICAL MEASUREMENT SYSTEM

BACKGROUND

Electrophysiology screening technologies are important for drug discovery. They are advanced due to automated, high-throughput electrophysiology measurement systems with large capacity libraries for screening and obtaining data to support drug discovery programs.

Ion channels play a key role in regulating many types of tissue functions. Ion channels themselves are regulated by both trans-membrane cation and anion gradients and dynamic changes in membrane potential, and they generate current as a useful index of their activity.

A typical high-throughput electrophysiology measurement system for ion channel screening comprises multiple first compartments, each compartment containing an aperture (or multiple apertures) connecting the first compartment to a second compartment. Furthermore, each first compartment contains a first electrode and the second compartment contains a second electrode. The electrodes are connected to an electrical data acquisition system. The compartments are filled with aqueous electrolyte solutions (first and second solutions respectively), and a biological membrane is positioned in the apertures, separating the first and the second compartments. By applying an electrical voltage across the electrodes and measuring currents through the electrodes electrophysiological properties of the biological membrane can be studied.

It has been noted that the electrodes utilized in such systems may not have a stable, well-defined electrochemical potential. Each electrode may be prone to have an electrical voltage error or voltage offset, in the range of up to several tens of millivolts (mV). In addition, voltage errors (or voltage offsets) may result due to electrochemical gradients between the first and second solutions (known also as junction potentials) that may reach values of one hundred millivolts or higher.

The electrical data acquisition system may not function appropriately when it includes a large number of channels (for example, 384 channels) and utilizes inexpensive, small, and low-power components, which may also have a tendency for electrical voltage offsets (voltage errors). Electrical voltage offsets from all of the channels may substantially aggravate voltage errors that compromise data acquisition.

To compensate for such voltage errors compensating circuitry may be incorporated into the data acquisition systems. The compensation circuitry may contain programmable digital-to-analog converters (trim DACs, or tDACs), one tDAC for each electrode/data channel. The tDACs are programmed to compensate for the voltage offsets. However, the requirements for tDACs are such that they are difficult to satisfy in multi-channel systems. The tDACs should have a sufficient resolution and a large enough voltage range to fully compensate for the voltage offsets. With a large number of channels, the cost and complexity of offset-compensating tDACs can become significant, packaging can become difficult, and reliability can suffer.

Therefore, there is a need for an improved approach to screening ion channels using a high-throughput measurement system with voltage offset correction.

SUMMARY

A computer-implemented method for controlling command voltages applied to electrodes during an electrophysiology measurement procedure using a high-throughput measurement system is provided. An initial command voltage is applied to the electrodes to obtain baseline currents respectively associated with the electrodes. A common offset voltage is determined based on the baseline currents, and an adjusted command voltage is determined based on the initial command voltage and the common offset voltage. The adjusted command voltage is applied to at least one of the electrodes to obtain an adjusted current measured by the electrode. A local offset voltage for the electrode is determined based on the adjusted current measured by the electrode. A subsequent command voltage applied to the electrode incorporates the common offset voltage and the local offset voltage.

A system for controlling command voltages applied to electrodes during an electrophysiology measurement procedure using a high-throughput measurement system is also provided. A sensing module is configured to apply command voltages to the electrodes, which measure respective baseline currents when the sensing applies an initial command voltage to the electrodes. A common offset voltage determination module determines a common offset voltage based on the baseline currents. An adjusted command voltage determination module determines an adjusted command voltage based on the initial command voltage and the common offset voltage. A local offset voltage determination module determines a local offset voltage for at least one of the electrodes based on an adjusted current measured by the electrode when the sensing module applies the adjusted command voltage to the electrode. A voltage control module configures the sensing module with the adjusted command voltage and the local offset voltage such that a subsequent voltage applied to the electrode incorporates the common offset voltage and the local offset voltage.

BRIEF DESCRIPTION OF THE FIGURES

These and other features, aspects, and advantages of the present invention will become better understood from the following description, statement of the invention, and accompanying figures where.

DETAILED DESCRIPTION

A high-throughput measurement system for performing electrophysiology measurements may include wells that contain multiple ion channels. Electrodes positioned within respective wells may sense ionic current passing through the ion channels. Each sense electrode is connected to a sensing module that applies an external voltage—i.e., a command voltage—between the electrodes. The sensing module may include voltage offset correction components such as: a trim DAC (tDAC) for providing a local offset voltage to an analog adder. A command DAC (cDAC) may provide the command voltages including an adjusted command voltage that incorporates a common offset voltage. The cDAC may also provide the adjusted command voltage to the analog adder, which may sum the local offset voltage and the adjusted command voltage such that the resulting command voltage incorporates the common offset voltage and the local offset voltage.

Figure 1:
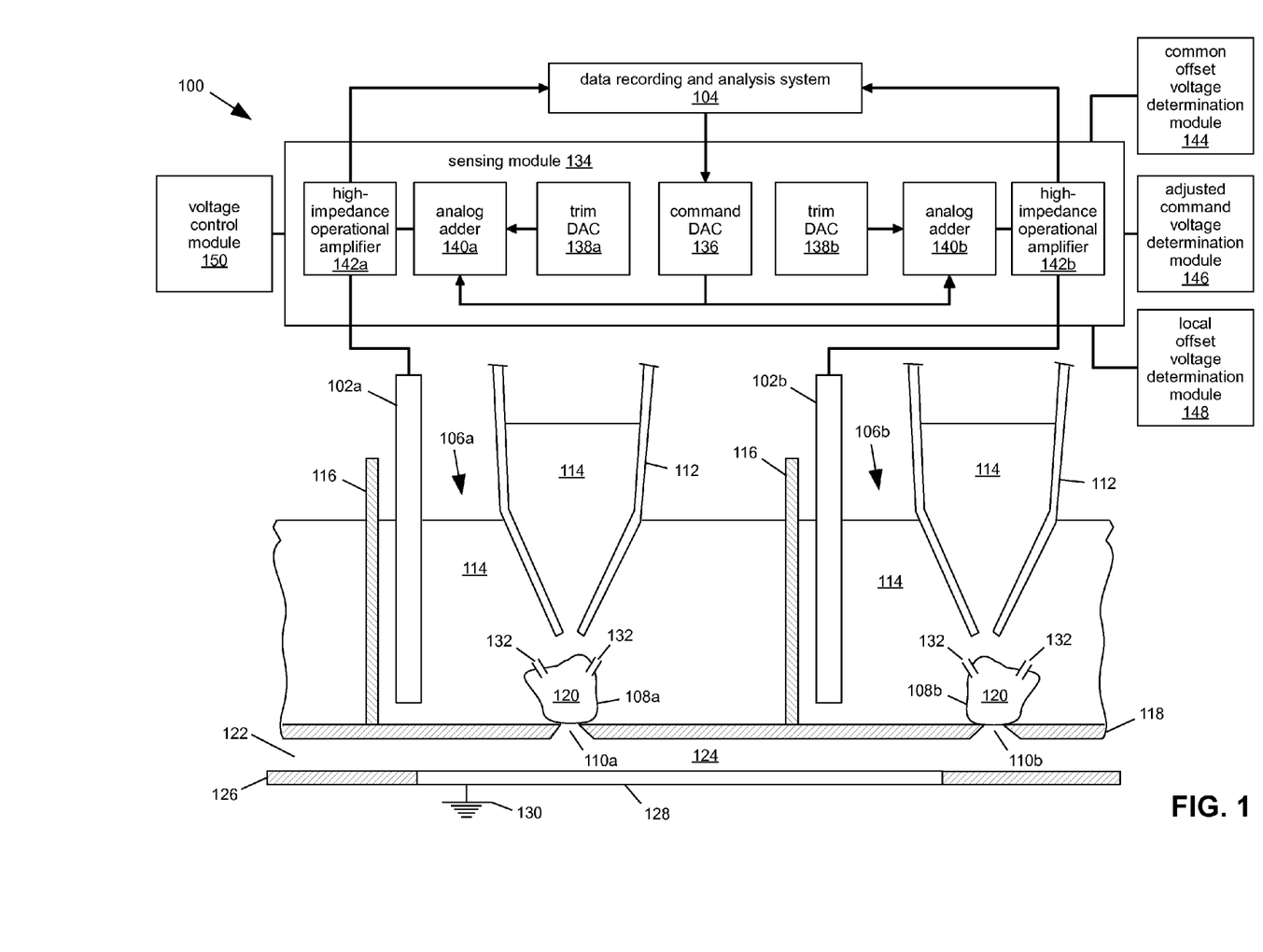
FIG. 1 is a schematic illustration of an example of an implementation of a high-throughput measurement system for controlling command voltages applied to electrodes during an electrophysiology measurement procedure.

Referring to FIG. 1, an example of an implementation of a high-throughput measurement system 100 for controlling command voltages applied to electrodes 102 during an electrophysiology measurement procedure is shown. The high-throughput measurement system 100 may include a data recording and analysis system 104 to record and analyze the ionic current activity occurring in multiple wells 106 that each include a cell 108 sealed to an aperture 110. A pipette 112 may deliver and remove fluid 114 from the well 106, and an electrode 102 may sense electrical signals in the well.

As seen in FIG. 1, two wells 106a and 106b are shown. Each well 106 is bounded by vertical structural members 116 and by a bottom horizontal structural member 118. The bottom horizontal member 118 includes multiple apertures 110 at each well 106 including an aperture 110a in well 106a and an aperture 110b in well 106b. During experiments, cells 108 are sealed to the individual apertures 110 that permit ionic coupling to the cell interior 120. In this example, cell 108a is sealed to aperture 110a and cell 108b is sealed to aperture 110b. A plenum 122 is positioned below the bottom horizontal member 118, which may hold a fluid 124, such as an intracellular fluid, during patch clamp experiments. The plenum 122 is bounded on the top by the horizontal member 118 and on the bottom by a parallel horizontal member 126 that includes one or more reference electrodes, e.g., reference electrode 128, which is electrically coupled to ground 130.

Each of the cells 108 may include multiple ion channels 132, which are evaluated for their response to stimuli in the individual wells 106. For example, a patch clamp assay may involve sensing a current flowing through the cells 108, more particularly the current flowing through ion channels 132 in the cells positioned in the wells 106 and having a membrane patch contacting the plenum 122.

In many assays, each stimulus is evaluated for its effect on the ability of the ion channel 132 to pass ionic current. The current is sensed by the electrodes 102 such as the electrode 102a in well 106a and electrode 102b in well 106b. The electrodes 102 may be, for example, silver/silver chloride (Ag/AgCl) electrodes, and the electrodes may provide an electrical connection to a sensing module 134 in response to a reversible exchange of chloride ions in the assay solution. An electric circuit may be completed via the reference electrode 128, which may also be, for example, an Ag/AgCl electrode.

In some example implementations, each electrode 102 may be respectively associated with its own sensing module 134. In other example implementations, however, the electrodes 102 may share some of the components of the sensing module 134 as shown by way of example in FIG. 1. The sensing module 134 may include: a command DAC 136; one or more tDACs 138; one or more analog adders 140; and one or more high-impedance operational amplifiers 142. The system 100 for controlling the command voltages applied to the electrodes 102, in this example, also includes: a common offset voltage determination module 144 that determines the common offset voltage; an adjusted command voltage determination module 146 that determines an adjusted command voltage; a local offset voltage determination module 148 that determines one or more local offset voltages; and a voltage control module 150 for controlling the voltages provided by the cDAC 136 and the tDACs 138 of the sensing module 134. As seen in FIG. 1, the common offset voltage determination module 144, the adjusted command voltage determination module 146, the local offset voltage determination module 148, and the voltage control module 150 are coupled to the sensing module 134 of the system 100.

As seen in FIG. 1, each electrode 102, in this example, is coupled to a respective high-impedance operational amplifier 142 that is configured to sense the current flowing in the electric circuit. The high-impedance operational amplifiers 142a and 142b, in this example, are also coupled to a data recording and analysis system 104 to record and analyze the electrical signals from the wells 106. A high electrical resistance seal between the aperture 110 and the cell membrane permits the current recorded by the amplifier 142 to be dominated by ions flowing through the cell membrane and not by ions flowing around the aperture directly into the well solution 114. The sensing module 134 is designed or configured to apply an external voltage—i.e., a command voltage—between the electrodes 102 and the reference electrode 128, thereby providing control of the trans-membrane voltage potential of the cells 108. As mentioned above, the sensing module 134 includes one or more trim DACs 138 for providing local offset voltages.

Also as seen in FIG. 1, the tDACs 138 are coupled to the respective analog adders 140. The wells 106, in this example, share the command DAC 136, which is also coupled to the analog adders 140. The cDAC 136 provides the command voltages including the adjusted command voltage that incorporates the common offset voltage. The voltage provided by the trim DACs 138 and the command DAC 136 is controlled, in this example, by a voltage control module 150 that is coupled to the sensing module 134. The analog adders 140 may sum the adjusted command voltage provided by the cDAC 136 and the respective local offset voltages provided by the tDACs 138 in order to provide a command voltage that incorporates both the common offset voltage and the local offset voltage.

The voltage control module 150 may configure the properties of the components of the sensing module 134 in order to make measurements and control the voltage provided by the cDAC 136 (e.g., the adjusted command voltage that incorporates the common voltage offset) and the voltage provided by the respective tDACs 138 (e.g., the respective local offset voltages). For example, the voltage control module 150 may program the cDAC 136 with the common offset voltage such that the cDAC provides a command voltage that incorporates the common offset voltage. The voltage control module 150 may also, for example, respectively program the tDACs 138 with the local offset voltages.

Figure 2A:
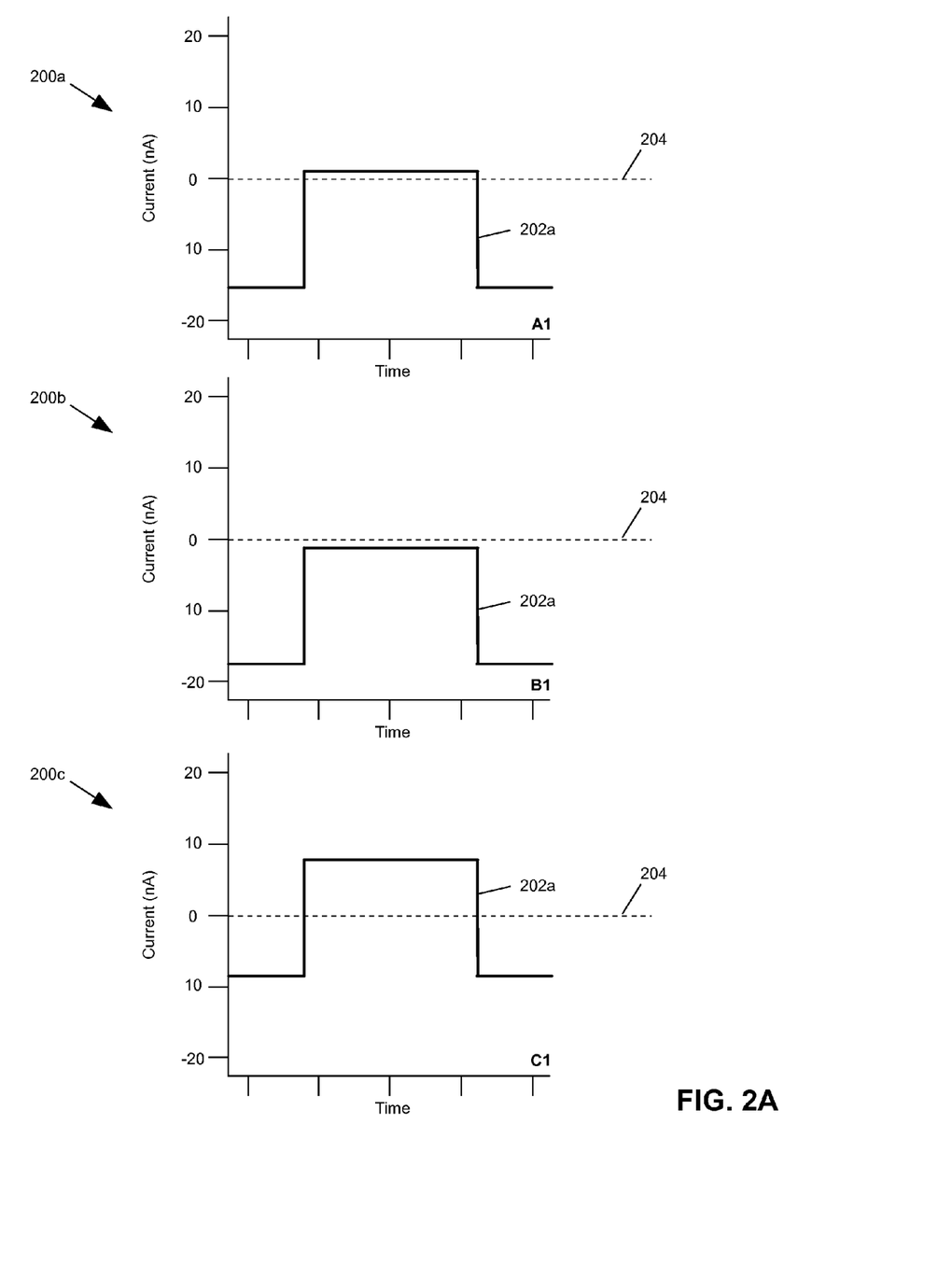
FIG. 2A illustrates three graphs for three baseline currents measured on three respective channels resulting from application of an initial command voltage.
Figure 2B:
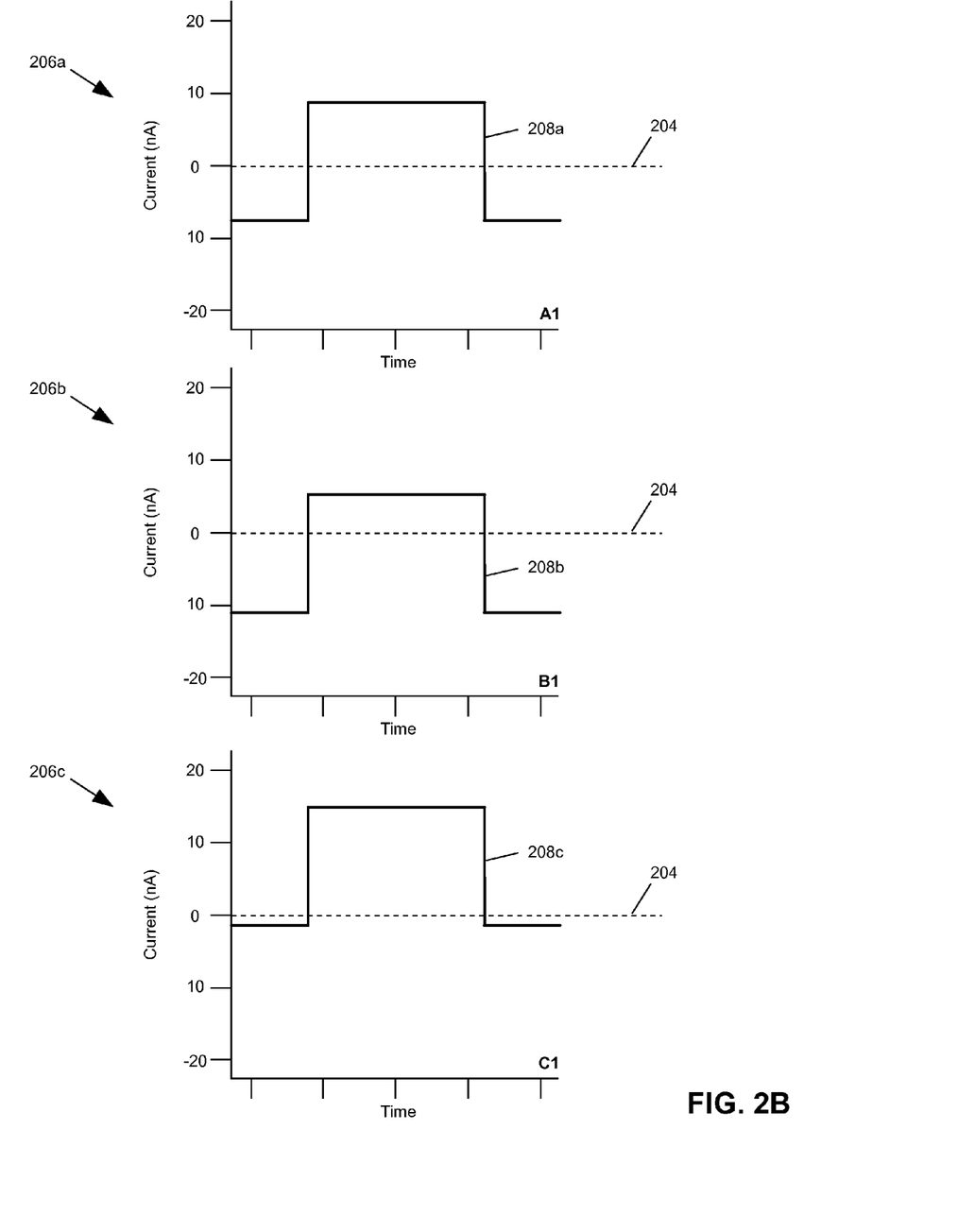
FIG. 2B illustrates three graphs for three adjusted currents measured on the three respective channels of FIG. 2A resulting from application of an adjusted command voltage.
Figure 2C:
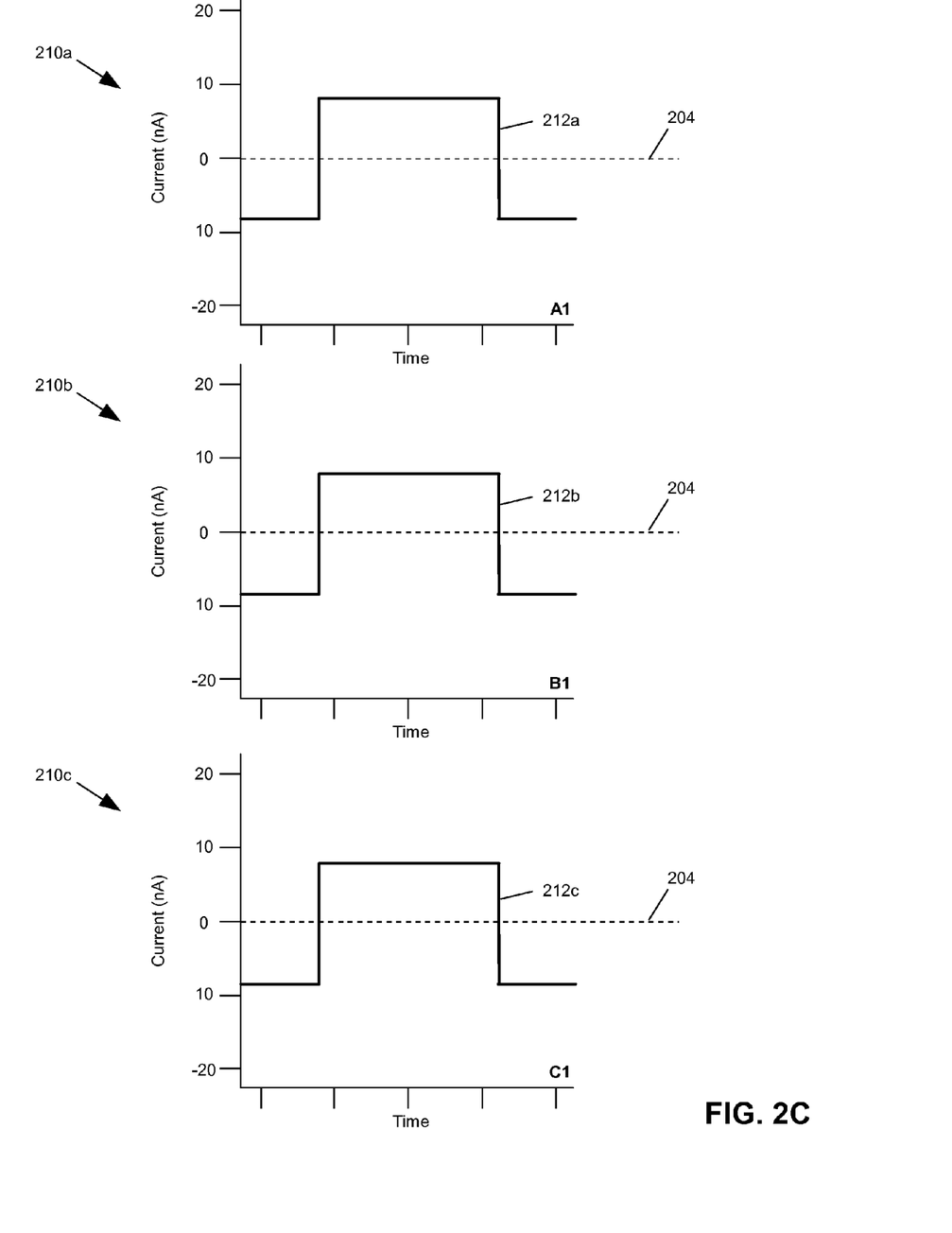
FIG. 2C illustrates three graphs for three subsequent currents measured on the three respective channels of FIG. 2A resulting from application of subsequent currents that include a common offset voltage and a local offset voltage.

Controlling the command voltages applied to the electrodes 102 will now be described with reference to FIGS. 2A-C. In FIGS. 2A-C, respective graphs 200 of current measurements 202 for three channels A1, B1 and C1 are shown. A multi-channel system, however, may include many more channels, e.g., 384 channels corresponding to 384 wells. Each graph 200 shows the measured currents 202 (measured in nanoamperes—nanoamps or nA) resulting from application of a command voltage to the electrode associated with the channel. The command voltage may be, for example, a voltage step, e.g., a voltage going from −25 mV to +25 mV and then returning back to −25 mV.

In FIG. 2A, the graphs 200a, 200b, and 200c illustrate the measured current 202 resulting from application of an initial command voltage. As seen in FIG. 2A, the measured currents 202a, 202b, and 202c are not consistently centered around a common midpoint 204 (e.g., zero). The measured current 202a for channel A1 and the measured current 202b for channel B1 are not centered on zero, the common midpoint 204 in this example. Accordingly, subsequent command voltages respectively applied to the electrodes of channels A1 and B1 should incorporate offset voltages in order to measure zero current, i.e., such that the subsequent current measurements are consistently centered around the common midpoint 204. The system 100 may determine a common offset voltage and respective local offset voltages such that subsequent currents are centered around a common midpoint as shown below with reference to FIG. 2C.

To determine the common offset voltage, the system 100 first applies an initial command voltage to obtain baseline current measurements (i.e., baseline currents) on the channels. Baseline currents 202 are shown by way of example in FIG. 2A. The common offset determination module 144 may determine the common offset voltage based on the baseline currents 202. Having obtained the baseline currents 202, the common offset determination module 144 may determine a respective offset current that is associated with the baseline current. The offset current may correspond to an amount of deviation from a central position such as, for example, zero. For example, as seen in FIG. 2A, the baseline current 202c on channel C1 goes from about −8 nA to about +8 nA and is thus centered around a zero-based central position. The respective baseline currents 202a and 202b for channel A1 and channel B1 are not centered around the zero-based central position, with the baseline current 202a going from about −15 nA to about +1 nA in channel A1 and the baseline current 202b going from about −17 nA to about −1 nA in channel 131. Accordingly, the offset currents for channel A1 and channel B1 may be determined, in this example, based on the amount that each baseline current 202 deviates from the central position—i.e., 7 nA for channel A1 and 10 nA for channel B1 for a zero-based central position.

The common offset voltage determination module 144, in this example, may then determine respective adjustment voltages associated with the offset currents. The adjustment voltage, in this example, corresponds to the voltage required to remove the offset current. To determine an adjustment voltage for an offset current of a channel, the common offset voltage determination module 144 may first determine the resistance (R) associated with the channel.

The common offset voltage determination module 144 may use Ohm's Law to determine the resistance associated with the channel:

$$R = V_i/I_b$$

where $V_i$ is the initial command voltage, $I_b$ is the baseline current 202 measured on the channel, and R is the resistance for the channel.

The common offset voltage adjustment determination module 144 may then determine the voltage adjustment for the channel—i.e., the voltage required to remove the offset current for the channel—also using Ohm's Law:

$$V_\alpha = R \times I_o$$

where R is the resistance for the channel, $I_o$ is the offset current for the channel, and $V_\alpha$ is the adjustment voltage required to remove the offset current.

The common voltage offset determination module 144, in this example, determines an adjustment voltage for multiple wells 106. In some example implementations, the common voltage offset determination module 144 may determine an adjustment voltage for each well 106 in the multi-well system. Having determined multiple adjustment voltages, the common voltage offset determination module 144 may calculate the average of the adjustment voltages. The average of the adjustment voltages may be, for example: the median of the adjustment voltages; the mean of the adjustment voltages; a minimized root-mean-square of the adjustment voltages; a peak-to-valley midpoint of the adjustment voltages; or other suitable measure of central tendency of the adjustment voltages. The common voltage offset determination module 144 may then identify the average of the adjustment voltages as the common offset voltage.

The adjusted command voltage determination module 146 may then determine an adjusted command voltage that incorporates the common offset voltage. For example, the adjusted command voltage determination module 146 may sum the initial command voltage and the common offset voltage in order to obtain the adjusted command voltage. The voltage control module 150 may then instruct the cDAC 136 to apply the adjusted command voltage to the electrodes in order to obtain adjusted current measurements (i.e., adjusted currents) on the channels.

In FIG. 213, the graphs 206a, 206b, and 206c illustrate the measured adjusted currents 208a, 208b, and 208c resulting from application of the adjusted command voltage that incorporates the common voltage offset. As seen in FIG. 2B, the measured adjusted currents 208a, 208b, and 208c have each moved by the same amount and in the same direction—about +8 nA in this example. As seen in FIG. 2B, however, each of the adjusted currents are still not consistently centered around a common midpoint 204. The local offset voltage determination module 148 determines a respective local offset voltage for each channel that may be utilized to consistently center each measured current around the common midpoint 204.

The local offset voltage determination module 148 may determine respective local offset voltages based on the adjusted currents 208 measured by the electrodes 102. The local offset voltage determination module 148 may determine a local offset voltage also using Ohm's Law:

$$V_l = R \times I_\alpha$$

where R is the resistance on the channel (as calculated above); $I_\alpha$ is the adjusted current measured by the electrode 102 on the channel; and $V_l$ is the local offset voltage. The local offset voltage determination module 148 may determine a respective local offset voltage for each channel (i.e., each electrode) of the multi-channel system in this manner. The voltage control module 150 may then program the tDACs 138 with the respective local offset voltages for the channels and may program the cDAC 136 with the common offset voltage. As discussed above, an analog adder 140 sums the adjusted command voltage provided by the cDAC 136 (which incorporates the common offset voltage) and the local offset voltage provided by the tDAC 138. As a result, a subsequent command voltage applied to the electrodes 102 incorporates both the common offset voltage and the local offset voltage. In this way, subsequent currents measured by electrodes 102 on each channel may be centered around a common midpoint, e.g., zero.

Referring to FIG. 2C, the graphs 210a, 210b, and 210c illustrate the subsequently measured currents 212a, 212b, and 212c resulting from application of the subsequent command voltages that incorporate the common offset voltage and that incorporate the respective local offset voltages for the channels. As seen in FIG. 2C, the subsequent currents 212 measured on each of the channels A1, B1, and C1 are each centered around the common midpoint 204, which, in this example, is zero. Thus, voltage errors are advantageously corrected and compensated for such that the measured currents are centered around a common midpoint.

Figure 3:
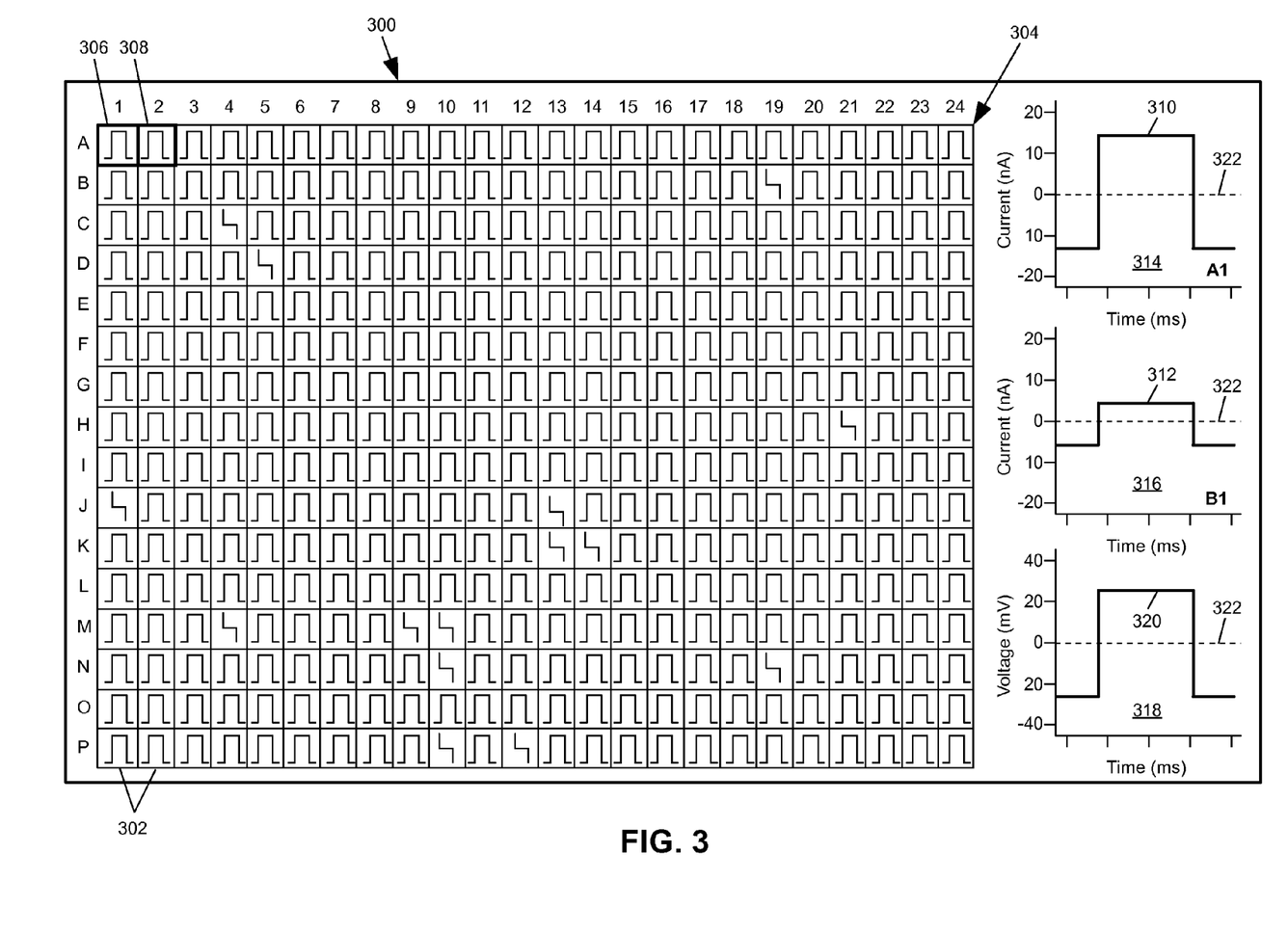
FIG. 3 is a portion of a screenshot that displays current measurements on a multi-channel high-throughput measurement system resulting from application of a command voltage.

Referring now to FIG. 3, a portion of a screenshot 300 that displays current measurements 302 on a multi-channel high-throughput measurement system resulting from application of a command voltage. In this example, the multi-channel system measures currents on 384 channels (channels A1-24, . . . , P1-24). The measured currents 302 for the channels are displayed in a selectable grid 304. In the example grid 304 of FIG. 3, channel A1 306 and channel A2 308 have been selected, and the measured currents 310 and 312 for channels A1 and A2 are respectively displayed in graphs 314 and 316 on the right-hand side of the display 300. The right-hand side of the display 300 also includes a graph 318 of the command voltage 320 applied to the channel electrodes. In this example, the command voltage 320 is a voltage step between −25 mV and +25 mV. The command voltage 320 applied to the electrode of channel A1, in this example, incorporates the common offset voltage and the local offset voltage for channel A1. Likewise, the command voltage applied to the electrode of channel A2 also incorporates the common offset voltage as well as the local offset voltage for channel A2. As a result, the current 310 measured on channel A1 and the current 312 measured on channel A2 are each centered around a common midpoint 322 (e.g., zero).

Figure 4:
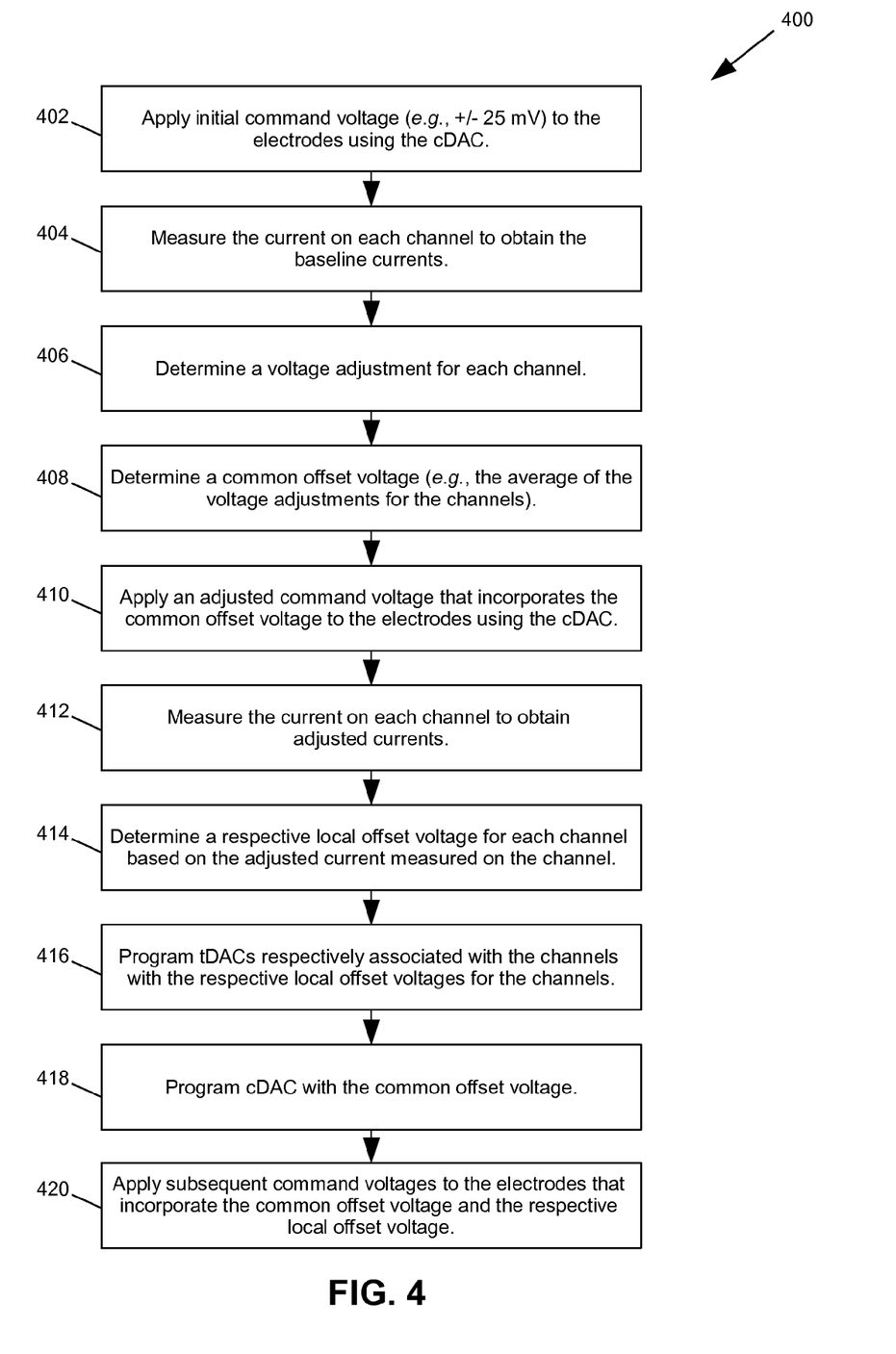
FIG. 4 is a flowchart of example method steps for controlling command voltages applied to electrodes during an electrophysiology measurement procedure using a high-throughput measurement system.

Referring now to FIG. 4, a flowchart 400 of example method steps for controlling command voltages applied to electrodes during an electrophysiology measurement procedure using a high-throughput measurement system is shown. An initial command voltage is applied to the electrodes using the cDAC (step 402). The current on each channel is then measured to obtain the baseline currents (step 404). A voltage adjustment for each channel is determined (step 406), and a common offset voltage is determined based on the voltage adjustments for the channels (step 408). The common offset voltage may be, for example, the average of the voltage adjustments for the channels.

An adjusted command voltage that incorporates the common offset voltage is then applied to the electrodes using the cDAC (step 410). The currents resulting from the application of the adjusted command voltage are then measured to obtain adjusted currents (step 412). A local offset voltage for each channel is then determined based on the adjusted current respectively measured on the channel (step 414). The tDACs associated with the channels are then programmed with the respective local offset voltages for the channels (step 416), and the cDAC is programmed with the common offset voltage (step 418). Subsequent command voltages may then be applied to the electrodes that incorporate both the common offset voltage and the respective local offset voltages (step 420).

It will be understood and appreciated that one or more of the processes, sub-processes, and process steps described in connection with FIGS. 1-4 may be performed by hardware, software, or a combination of hardware and software on one or more electronic or digitally-controlled devices. The software may reside in a software memory (not shown) in a suitable electronic processing component or system such as, for example, one or more of the functional systems, devices, components, modules, or sub-modules schematically depicted in FIGS. 1-4. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module (e.g., the voltage control module 150, common offset voltage determination module 144, adjusted command voltage determination module 146, and local offset voltage determination module 148 of FIG. 1), which includes, for example, one or more microprocessors, general purpose processors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "coupled" as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A computer-implemented method for controlling command voltages applied to a plurality of electrodes during an electrophysiology measurement procedure using a high-throughput measurement system, the method comprising:
    applying an initial command voltage to the plurality of electrodes to obtain a plurality of baseline currents respectively associated with the plurality of electrodes;
    determining a common offset voltage based, at least in part, on the plurality of baseline currents;
    determining an adjusted command voltage based on the initial command voltage and the common offset voltage;
    applying the adjusted command voltage to at least one of the electrodes to obtain an adjusted current measured by the at least one electrode;
    determining a local offset voltage for the at least one electrode based, at least in part, on the adjusted current measured by the at least one electrode;
    configuring a sensing module coupled to the at least one electrode with the adjusted command voltage and the local offset voltage by programming a command digital-to-analog converter (cDAC) coupled to the at least one electrode with the adjusted command voltage and programming a trim digital-to-analog converter (tDAC) coupled to the at least one electrode with the local offset voltage; and
    wherein a subsequent command voltage applied to the at least one electrode incorporates the common offset voltage and the local offset voltage.

2. The computer-implemented method of claim 1, further comprising:
    summing the initial command voltage and the common offset voltage to obtain the adjusted command voltage; and
    summing the adjusted command voltage and the local offset voltage to obtain the subsequent command voltage for the at least one electrode.

3. The computer-implemented method of claim 1, further comprising:
    respectively applying a plurality of subsequent command voltages to the plurality of electrodes such that subsequent currents respectively measured by the plurality of electrodes are each centered around a common midpoint; and
    transmitting the subsequent currents to a data recording and analysis system via a plurality of channels respectively associated with the plurality of electrodes.

4. The computer-implemented method of claim 3, wherein:
    the plurality of electrodes are respectively positioned within a plurality of wells to measure ionic current activity respectively occurring at the plurality of wells; and
    the subsequent currents respectively correspond to the ionic current activity occurring at the plurality of wells.

5. The computer-implemented method of claim 1, wherein determining the common offset voltage includes:
    obtaining a plurality of offset currents respectively associated with the plurality of baseline currents;
    determining a plurality of adjustment voltages respectively associated with the plurality of offset currents;
    determining an average of the plurality of adjustment voltages; and
    identifying the average of the plurality of adjustment voltages as the common offset voltage.

6. The computer-implemented method of claim 5, wherein:
    individual offset currents in the plurality of offset currents respectively correspond to an amount of deviation from a central position; and
    individual adjustment voltages in the plurality of adjustment voltages respectively correspond to a voltage required to remove the offset current associated with the individual adjustment voltage.

7. The computer-implemented method of claim 5, wherein individual adjustment voltages in the plurality of adjustment voltages are determined based on:
    the initial command voltage;
    the offset current associated with the individual adjustment voltage; and
    the baseline current associated with the offset current that is associated with the individual adjustment current.

8. The computer-implemented method of claim 5, wherein the average of the plurality of adjustment voltages is selected from the group consisting of:
    a median of the plurality of adjustment voltages;
    a mean of the plurality of adjustment voltages;
    a minimized root-mean-square of the plurality of adjustment voltages; and
    a peak-to-valley midpoint of the plurality of adjustment voltages.

9. A high-throughput measurement system for controlling command voltages applied to a plurality of electrodes during an electrophysiology measurement procedure comprising:
    a sensing module comprising a command digital-to-analog converter (cDAC) coupled to individual electrodes in the plurality of electrodes for providing the command voltages, and a trim digital-to-analog converter (tDAC) coupled to the at least one electrode for providing the local offset voltage, wherein the sensing module is configured to apply command voltages to the plurality of electrodes whereby the plurality of electrodes respectively measure a plurality of baseline currents when the sensing module applies an initial command voltage to the plurality of electrodes;
    a common offset voltage determination module that determines a common offset voltage based, at least in part, on the plurality of baseline currents;
    an adjusted command voltage determination module that determines an adjusted command voltage based on the initial command voltage and the common offset voltage;
    a local offset voltage determination module that determines a local offset voltage for at least one of the electrodes based, at least in part, on an adjusted current measured by the electrode when the sensing module applies the adjusted command voltage to the electrode; and
    a voltage control module that configures the sensing module with the adjusted command voltage and the local offset voltage such that a subsequent command voltage applied to the electrode incorporates the common offset voltage and the local offset voltage.

10. The system of claim 9, wherein the sensing module further includes an analog adder coupled to the cDAC and coupled to the tDAC wherein the analog adder sums the adjusted command voltage provided by the cDAC and the local offset voltage provided by the tDAC in order to obtain the subsequent command voltage applied to the at least one electrode.

11. The system of claim 9, wherein the adjusted command voltage determination module sums the initial command voltage and the common offset voltage to obtain the adjusted command voltage.

12. The system of claim 9, wherein:
the sensing module respectively applies a plurality of subsequent command voltages to the plurality of electrodes such that subsequent currents respectively measured by the plurality of electrodes are each centered around a common midpoint; and
the subsequent currents are transmitted to a data recording and analysis system via a plurality of channels respectively associated with the plurality of electrodes.

13. The system of claim 12, wherein:
the plurality of electrodes are respectively positioned within a plurality of wells to measure ionic current activity respectively occurring at the plurality of wells; and
the subsequent currents respectively correspond to the ionic current activity occurring at the plurality of wells.

14. The system of claim 9, wherein the common offset voltage determination module:
obtains a plurality of offset currents respectively associated with the plurality of baseline currents;
determines a plurality of adjustment voltages respectively associated with the plurality of offset currents;
determines an average of the plurality of adjustment voltages; and
identifies the average of the plurality of adjustment voltages as the common offset voltage.

15. The system of claim 14, wherein:
individual offset currents in the plurality of offset currents respectively correspond to an amount of deviation from a central position; and
individual adjustment voltages in the plurality of adjustment voltages respectively correspond to a voltage required to remove the offset current associated with the individual adjustment voltage.

* * * * *